United States Patent
Coman

(10) Patent No.: US 10,267,946 B2
(45) Date of Patent: Apr. 23, 2019

(54) MAGNETIC RESONANCE PULSE SEQUENCES HAVING WAIT TIMES BASED ON CARRIER SPEED

(71) Applicant: Radu Coman, Hannover (DK)

(72) Inventor: Radu Coman, Hannover (DK)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 314 days.

(21) Appl. No.: 15/170,519

(22) Filed: Jun. 1, 2016

(65) Prior Publication Data

US 2017/0351002 A1  Dec. 7, 2017

(51) Int. Cl.
| | | |
|---|---|---|
| *G01V 1/00* | (2006.01) | |
| *G01V 3/32* | (2006.01) | |
| *G01V 3/38* | (2006.01) | |
| *G01N 1/00* | (2006.01) | |
| *G01R 1/00* | (2006.01) | |

(52) U.S. Cl.
CPC .................. *G01V 3/32* (2013.01); *G01V 3/38* (2013.01); *G01N 1/00* (2013.01); *G01R 1/00* (2013.01); *G01V 2200/00* (2013.01)

(58) Field of Classification Search
CPC .. G01V 1/00; G01V 2200/00; G01N 2201/00; G01R 1/00
See application file for complete search history.

(56) References Cited

U.S. PATENT DOCUMENTS

| | | |
|---|---|---|
| 6,140,817 A | 10/2000 | Flaum et al. |
| 6,140,818 A | 10/2000 | Hurlimann |
| 6,229,308 B1 | 5/2001 | Freedman |
| 6,232,778 B1 | 5/2001 | Speier et al. |
| 6,369,567 B1 | 4/2002 | Song et al. |
| 6,392,409 B1 | 5/2002 | Chen |
| 6,512,371 B2 | 1/2003 | Prammer |

(Continued)

OTHER PUBLICATIONS

Hou, et al.; "Determining Fluid Volume in Gas and/or Light Oil Reservoirs: Using a New Triple-Wait-Time NMR Logging Method"; 2000; Internet; URL: http://dialog.proquest.com; 2 pgs.

(Continued)

*Primary Examiner* — Jermele M Hollington
*Assistant Examiner* — Temilade Rhodes-Vivour
(74) *Attorney, Agent, or Firm* — Cantor Colburn LLP

(57) ABSTRACT

An embodiment of a nuclear magnetic resonance (NMR) apparatus for estimating properties of an earth formation includes an NMR measurement device including a transmitting assembly configured to emit a pulse sequence and a receiving assembly configured to detect an echo train based on the pulse sequence, and a processor. The processor is configured to perform receiving input parameters including an axial speed of the NMR measurement device and a $T_1$ value associated with a selected formation fluid, analyzing polarization data associated with the $T_1$ value, the polarization data describing a dependency between polarization and axial speed, determining a wait time for the pulse sequence based on the polarization data, applying the pulse sequence with the determined wait time to the transmitting assembly, and estimating a property of the earth formation based on the echo train detected by the receiving assembly in response to the pulse sequence.

20 Claims, 6 Drawing Sheets

(56) References Cited

U.S. PATENT DOCUMENTS

| | | | |
|---|---|---|---|
| 6,600,316 B2 | 7/2003 | Chen et al. | |
| 6,661,226 B1 | 12/2003 | Hou et al. | |
| 6,703,832 B2 | 3/2004 | Heaton et al. | |
| 6,972,564 B2 | 12/2005 | Chen et al. | |
| 7,135,862 B2 | 11/2006 | Hagiwara | |
| 7,196,516 B2 | 3/2007 | Blanz et al. | |
| 7,199,580 B2 | 4/2007 | Akkurt | |
| 7,358,725 B2 | 4/2008 | Blanz | |
| 7,565,246 B2 | 7/2009 | Fang et al. | |
| 8,131,469 B2 | 3/2012 | Chen et al. | |
| 8,831,885 B2 | 9/2014 | Lan et al. | |
| 9,222,902 B2 | 12/2015 | Gruber et al. | |
| 9,360,588 B2* | 6/2016 | Young | G01V 1/00 |
| 2004/0183533 A1* | 9/2004 | Edwards | G01N 24/081 |
| | | | 324/303 |
| 2005/0162162 A1* | 7/2005 | Itskovich | G01V 3/32 |
| | | | 324/303 |
| 2009/0066327 A1* | 3/2009 | Chen | G01N 24/081 |
| | | | 324/303 |
| 2013/0060474 A1 | 3/2013 | Venkataramanan et al. | |
| 2015/0145513 A1 | 5/2015 | Li et al. | |
| 2015/0293195 A1* | 10/2015 | Jachmann | G01N 24/081 |
| | | | 324/303 |
| 2016/0018555 A1 | 1/2016 | Jachmann et al. | |
| 2016/0047936 A1* | 2/2016 | Ali | G01V 3/32 |
| | | | 324/303 |

OTHER PUBLICATIONS

Moritz, Craig; "NMR Tools Afford New Logging Choices"; Apr. 17, 2000; Oil & Gas Journal Internet; Retrieved from the Internet URL: http://www.ogj.com/articles/print/volume-98/issue016/in-this-issue/production/nmr-to . . . ; 16 pages.

Stambaugh; "NMR Tools Afford New Logging Choices"; 2000; Internet; URL: http://dialog.proquest.com; 10 pgs.

Xin, et al.; "Analysis and optimization of pre-polarization methodology for NMR logging"; 2014; Internet; URL: http://dialog.proquest.com; 2 pgs. Abstract only, article only in chinese, we do not have translation of the article.

* cited by examiner

US 10,267,946 B2

MAGNETIC RESONANCE PULSE SEQUENCES HAVING WAIT TIMES BASED ON CARRIER SPEED

BACKGROUND

Understanding the characteristics of geologic formations and fluids located therein is important for effective hydrocarbon exploration and production. Formation evaluation relies on accurate petrophysical interpretation derived from a diverse set of logging technologies. One such technology, nuclear magnetic resonance (NMR), can be used to estimate formation characteristics such as porosity and permeability of rocks, to perform fluid typing and determine fluid volumes, and to estimate fluid characteristics such as viscosity.

SUMMARY

An embodiment of a nuclear magnetic resonance (NMR) apparatus for estimating properties of an earth formation includes a carrier configured to be deployed in a borehole in the earth formation, an NMR measurement device including a transmitting assembly configured to emit a pulse sequence and a receiving assembly configured to detect an echo train based on the pulse sequence, and a processor configured to communicate with the NMR measurement device. The processor is configured to perform receiving input parameters including an axial speed of the NMR measurement device and a $T_1$ value associated with a selected formation fluid, analyzing polarization data associated with the $T_1$ value, the polarization data describing a dependency between polarization and axial speed, determining a wait time for the pulse sequence based on the polarization data, applying the pulse sequence with the determined wait time to the transmitting assembly, and estimating a property of the earth formation based on the echo train detected by the receiving assembly in response to the pulse sequence.

An embodiment of a method of performing a nuclear magnetic resonance (NMR) measurement includes receiving input parameters at a processor in communication with an NMR measurement device, the input parameters including an axial speed of the NMR measurement device and a $T_1$ value associated with a selected formation fluid, the NMR measurement device including a transmitting assembly configured to emit a pulse sequence into an earth formation. The method also includes analyzing polarization data associated with the $T_1$ value, the polarization data describing a dependency between polarization and axial speed, determining a wait time for the pulse sequence based on the polarization data, applying the pulse sequence with the determined wait time to the transmitting assembly, and estimating a property of the earth formation based on an echo train detected by the NMR measurement device in response to the pulse sequence.

BRIEF DESCRIPTION OF THE DRAWINGS

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

DETAILED DESCRIPTION

Methods, systems and apparatuses for measuring characteristics of an earth formation using magnetic resonance techniques are described herein. Embodiments of nuclear magnetic resonance (NMR) apparatuses, systems and methods utilize pulse sequences having wait times that are estimated or selected based at least on logging speed, which is defined as the speed or velocity of a component (e.g., a NMR tool, a wireline tool, a logging-while-drilling tool, a drilling assembly, etc.) along the path or axis of a borehole.

An embodiment of an NMR apparatus or system includes or is connected to a processor that is configured select a wait time for a pulse sequence based on a $T_1$ value of a formation fluid and a measured or expected logging speed. In one embodiment, the $T_1$ value is associated with a so-called "long-$T_1$ fluid". Examples of long-T fluids include moveable water and light hydrocarbons (e.g., light oil and gas), which can be distinguished from fluids having a shorter $T_1$ (referred to as "short-$T_1$ fluids), such as heavy oil and bound water. "Wait time" is defined, in one embodiment, as the time during which the NMR-activated material (earth formation) is polarized, i.e. magnetized. The processor receives input data including the $T_1$ value of a fluid such as a long-$T_1$ fluid ($T_{1\lambda}$), a target polarization, and an expected or measured logging speed, and estimates the wait time or selects the wait time from a plurality of pre-defined wait times based on the input data. Selection of wait times as described herein can result in more accurate NMR measurements and shorter wait times than conventional NMR measurement techniques.

Figure 1:
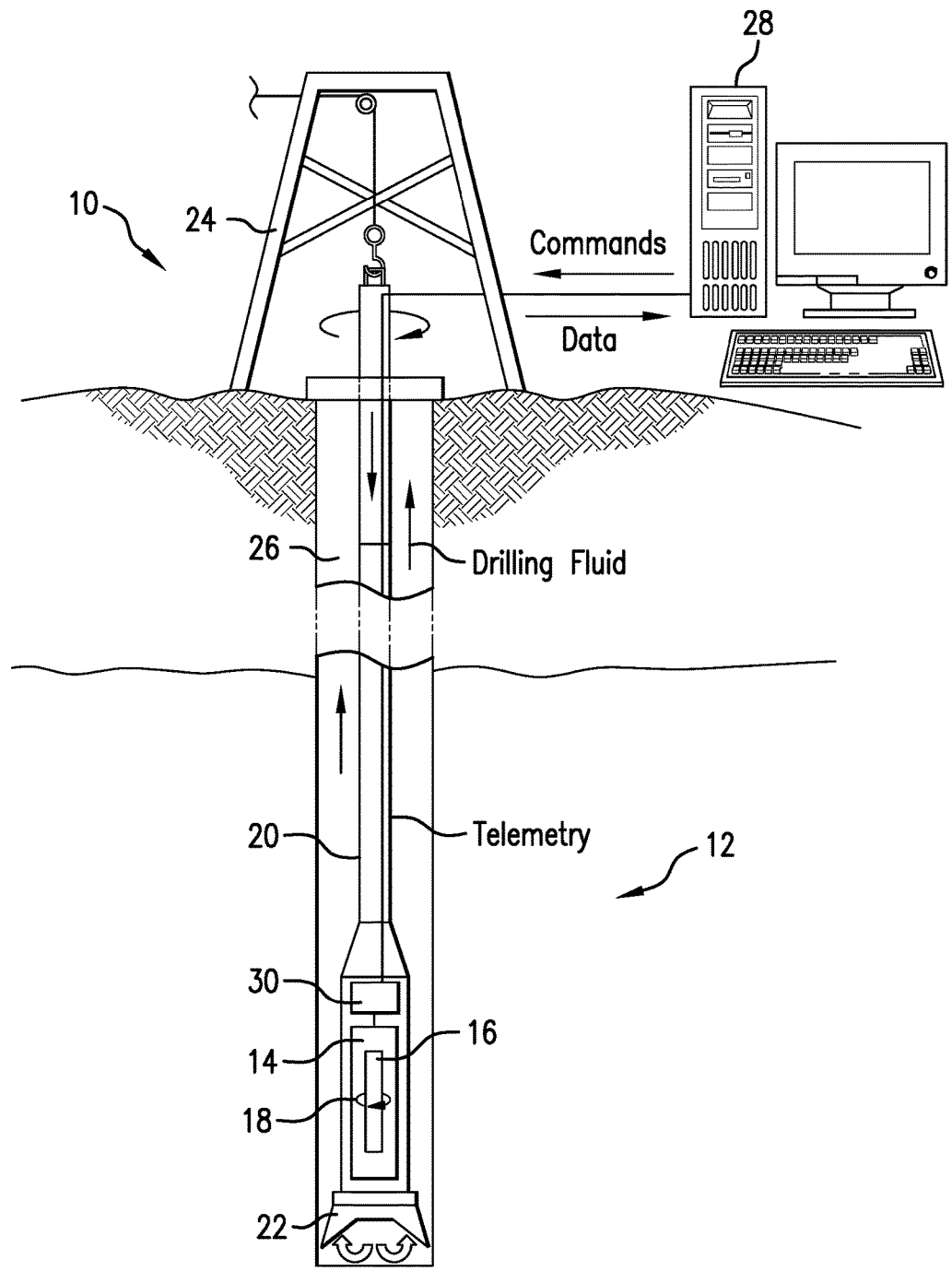
FIG. 1 depicts an embodiment of a formation measurement system that includes a nuclear magnetic resonance (NMR) measurement apparatus.

FIG. 1 illustrates an exemplary embodiment of a downhole measurement, data acquisition, and/or analysis system 10 that includes devices or systems for in-situ measurement of characteristics of an earth formation 12. The system 10 includes a magnetic resonance apparatus such as an NMR tool 14. An example of the magnetic resonance apparatus is a logging-while-drilling (LWD) magnetic resonance tool. The tool 14 is configured to generate magnetic resonance data for use in estimating characteristics of a formation, such as porosity, irreducible water saturation, permeability, hydrocarbon content, and fluid viscosity.

An exemplary tool 14 includes a static magnetic field source 16, such as a permanent magnet assembly, that magnetizes formation materials and a transmitter and/or receiver assembly 18 (e.g., an antenna or antenna assembly) that transmits radio frequency (RF) energy or pulsed energy that generates an oscillating magnetic field in the formation, and detects NMR signals as voltages induced in the receiver. The transmitter assembly 18 may serve the receive function, or distinct receiving antennas may be used for that purpose. It can be appreciated that the tool 14 may include a variety of components and configurations as known in the art of nuclear magnetic resonance or magnetic resonance imaging.

The tool 14 may be configured as a component of various subterranean systems, such as wireline well logging and LWD systems. For example, the tool 14 can be incorporated within a drill string 20 including a drill bit 22 or other suitable carrier and deployed downhole, e.g., from a drilling rig 24 into a borehole 26 during a drilling operation. The tool 14 is not limited to the embodiments described herein, and may be deployed in a carrier with alternative conveyance methods. A "carrier" as described herein means any device, device component, combination of devices, media and/or member that may be used to convey, house, support or otherwise facilitate the use of another device, device component, combination of devices, media, and/or member. Exemplary non-limiting carriers include drill strings of the coiled tube type, of the jointed pipe type, and any combination or portion thereof. Other carrier examples include casing pipes, wired pipes, wirelines, wireline sondes, slickline sondes, drop shots, downhole subs, bottom-hole assemblies, and drill strings.

In one embodiment, the tool 14 and/or other downhole components are equipped with transmission equipment to communicate ultimately to a surface processing unit 28. Such transmission equipment may take any desired form, and different transmission media and methods may be used, such as wired, fiber optic, mud pulse telemetry and/or other wireless transmission methods. Additional processing units may be deployed with the carrier. For example, a downhole electronics unit 30 includes various electronic components to facilitate receiving signals and collect data, transmitting data and commands, and/or processing data downhole. The surface processing unit 28, electronics 30, the tool 14, and/or other components of the system 10 include devices as necessary to provide for storing and/or processing data collected from the tool 14 and other components of the system 10. Exemplary devices include, without limitation, at least one processor, storage, memory, input devices, output devices, and the like.

Magnetic resonance measurements are performed by the NMR tool 14, which generates a static magnetic field ($B_0$) in a volume within the formation (a "volume of interest") using one or more magnets (e.g., the magnetic field source 16). An oscillating (e.g., RF) magnetic field ($B_1$) is generated, which is at least substantially perpendicular to the static magnetic field in the volume of interest. The volume of interest may be circular or toroidal around the borehole, and/or focused or directed toward a specific angular region (i.e., side-looking).

The surface processing unit 28, electronics 30 and/or other suitable processing device includes a processor configured to generate electrical pulses and transmit the pulses to the transmitter assembly, which in turn generates pulses of electromagnetic energy that induce the oscillating field $B_1$ in the volume of interest. Such a processing device may be referred generally as a pulse generator, which includes a microcontroller or other processor that is capable of transmitting a pulse sequence or series of pulse sequences. Each pulse sequence can be programmed or set based on parameters such as pulse duration, time intervals between pulses and time between successive pulse sequences (wait time).

When exposed to the magnetic field $B_0$, the spin axes of hydrogen nuclei in the formation precess around the direction of the $B_0$ field with the Larmor frequency, which is proportional to the strength of the magnetic field $B_0$. Over time, the spin axes align themselves at distinct angles along the $B_0$ field and create a net magnetization (i.e., polarization), which will build up with the time constant $T_1$, referred to as a longitudinal relaxation or spin lattice relaxation time. $T_2$ is a time constant of the transversal relaxation, which describes the loss of magnetization in the plane orthogonal to the $B_0$ field.

When the $B_1$ field is turned on, the magnetization will be rotated around the $B_1$ field by an angle proportional to the length of the pulse and to the strength of the $B_1$ field. Ideally, the $B_1$ field is oriented perpendicular to the $B_0$ field in the volume of interest, e.g., in the x-y plane orthogonal to the longitudinal or z-axis, where the z-axis points along $B_0$ in the volume of interest.

In one embodiment, the tool is configured as a low gradient NMR tool that generates a static magnetic field that has a gradient that is sufficiently low so that the apparent $T_1$ is similar to the apparent T2. Such low gradient fields are much less sensitive to the molecular diffusion than typical high gradient fields. An exemplary static magnetic field for a low gradient tool is less than or equal to about 10 G/cm (Gauss per centimeter). In another example, a low gradient tool is less than or equal to about 5 G/cm.

The processing device performs an acquisition method that controls how an NMR logging tool measures the NMR properties of a formation. The acquisition method includes several measurements, with each measurement built from the application of the $B_1$ field as a sequence of short-duration pulses, referred to as a "pulse sequence" or "data gathering sequence". The pulses may be rectangular or other shaped. A pulse sequence is used to measure $T_2$ relaxation, and may be indirectly used for the measurement of the $T_1$ relaxation. In an embodiment of a pulse sequence, the first pulse is a "tipping pulse", which acts to align the nuclear magnetization in the formation in a direction perpendicular to the static field $B_0$, e.g., rotate the magnetization from the z-direction into the x-y plane. After the tipping pulse, the nuclear magnetization disperses in the x-y plane due to a spread of precession frequencies caused by $B_0$ field inhomogeneity and gradually returns or "relaxes" to its alignment with the static field.

At a selected time after the tipping pulse, one or more "refocusing pulses" are applied, which have a duration and amplitude selected to at least partly reverse the magnetizations of microscopic volume elements. In consequence the coherent macroscopic magnetization that was lost after the tipping pulse rephases after each refocus pulse, resulting in so-called spin echoes that induce a measurable voltage in the receiving antenna.

Pulse sequence parameters include wait time (TW), echo spacing or inter-echo time (TE), the number of echoes (NE) produced by a sequence, and the number of successive repeated pulse sequences. The wait time is the period of time between the last pulse of a saturation sequence and the first pulse of the data gathering sequence (i.e., the tipping pulse). In some cases a saturation sequence is not used, and the wait time is the time between successive data gathering sequences, e.g., the last pulse of a previous data gathering sequence and the first pulse of a current data gathering sequence.

An example of a pulse sequence that can be applied by the NMR tool is a Carr-Purcell-Meiboom-Gill (CPMG) pulse sequence, which has a constant time between the refocus pulses. Note that, for a CPMG pulse sequence, the inter-pulse time interval is the same as the inter-echo time interval, TE, where TE is measured between centers of echoes or centers of refocus pulses. The CPMG sequence begins with a tipping pulse followed by a series of refocusing pulses. MR echoes occur halfway between the refocusing pulses at equidistant times (TE).

Pulse sequences can include $T_2$ pulse sequences, where the number of recorded echoes is related to the wait time. Pulse sequences can also include $T_1$ pulse sequences, where only few echoes are recorded for various wait times. In the following description, a "pulse sequence" refers to a $T_2$ pulse sequence.

Each pulse sequence has a wait time selected for one of various purposes. Each pulse sequence can have the same wait time, or one or more of a series of pulse sequences can have different wait times (e.g., as part of a set of dual-wait-time or DTW data acquisition method or technique). For example, a pulse sequence may have a relatively long wait time ($TW_L$) or one or more relatively short wait times ($TW_S$) that are shorter than the long wait time. A sequence having a long wait time is referred to as a "long-TW sequence" and a measurement using the long-TW sequence is referred to as a "long measurement".

The main objective of a long measurement is to provide the total porosity. This objective is achieved if all fluids in the formation are sufficiently polarized at the end of the wait time. In one embodiment, the long wait time ($TW_L$) is a period of time which is needed to fully polarize the movable pore fluid in a sensitive volume or polarize the fluid to a target polarization factor (or shortly "polarization"). A typical target polarization is at least 95%. Other wait times (short wait times) include, for example, a clay bound water (CBW wait time) which is selected to fully polarize only porosity components with short $T_1$ times.

Wait times are typically selected based on the $T_1$ value, which is different for different types of fluids in porous formations. For example, water usually has a lower $T_1$ value than oil, and oil usually has a lower $T_1$ than gas. As described herein, fluids can be classified as short-$T_1$ fluids such as bound water (e.g., CBW) and/or heavy oil, and long-$T_1$ fluids such as moveable water or free fluid, or light oil and gas. As described herein, "$T_{1\lambda}$" is the $T_1$ value of a long-$T_1$ fluid.

Conventional NMR measurements select wait times based on the $T_1$ value of one or more fluids without considering logging speed. For example, in conventional NMR measurements, the long wait time is selected by considering only the expected $T_1$ value of a long-$T_1$ fluid (the $T_{1\lambda}$ value) and neglect the influence of the logging speed on the polarization. Under this assumption, the wait time is typically set to be at least 3 times $T_{1\lambda}$.

For a stationary measurement with perfect saturation, the polarization factor, a, is expressed by the following equation:

$$a = 1 - e^{-\frac{tw}{T_{1\lambda}}},$$

where $T_{1\lambda}$ is the wait time.

However, if the logging tool is moving, then the polarization factor depends not only on $T_{1\lambda}$ and wait time, but also on the logging speed ($v_a$), the $B_0$ field, and the initial magnetization, $M_z^0$, at the start of the wait time. The initial magnetization depends on logging speed, tool design, and saturation sequence design. The polarization factor includes the polarization enhanced by tool motion as well as polarization reduced by a finite wait time.

For an axially moving tool, the conventionally set wait time may not be optimal and can lead to a porosity overcall, which can be higher than 30%. For example, a low magnetic field gradient NMR logging tool is affected by the so-called enhanced-polarization effect. This effect is especially significant for fluids with large $T_1$ values and for elevated logging speeds.

An NMR measurement device or tool includes or is connected to a processing device (e.g., the surface processing unit 28 and/or electronics 30) that is configured to perform NMR measurements using wait times that are selected or estimated based not only on the $T_1$ value of one or more fluids, but also on the logging speed of the NMR tool and/or other downhole component. The processing device may perform both wait time selection and control of the NMR transmitter, or be connected to a pulse generator or other control device.

The processing device, individually or in combination with other devices or processors, performs various functions including performing NMR measurements and/or estimating formation properties, which include generating pulses of electromagnetic energy that induce the oscillating $B_1$ field in a volume of interest. Acquisition of NMR data is performed using a wait time (TW) that is calculated based on a logging speed and/or an expected logging speed. As described herein, the "logging speed" refers to the axial motion of a NMR tool along an axis of a borehole. The logging speed may correspond to the logging speed in wireline applications or the rate of penetration (ROP) in while-drilling applications.

The wait time is estimated or selected based on polarization data that relates the polarization of a fluid due to the $B_0$ field to logging speed. The polarization data may come in any suitable form and be derived from any suitable source, such as experimental data, data from prior operations (e.g., in a current borehole, in another borehole in the formation such as an offset well, or in a similar formation), and modeling. In one embodiment, the wait time is selected or estimated based on a polarization map or similar data set or representation. It is noted that the polarization of the fluid is not only dependent on logging speed and $B_0$, but also dependent on other factors such as tool design ($B_0$ field distribution) and on acquisition design (efficiency of the saturation sequence). These additional factors may be considered as part of the polarization data.

Figure 2:
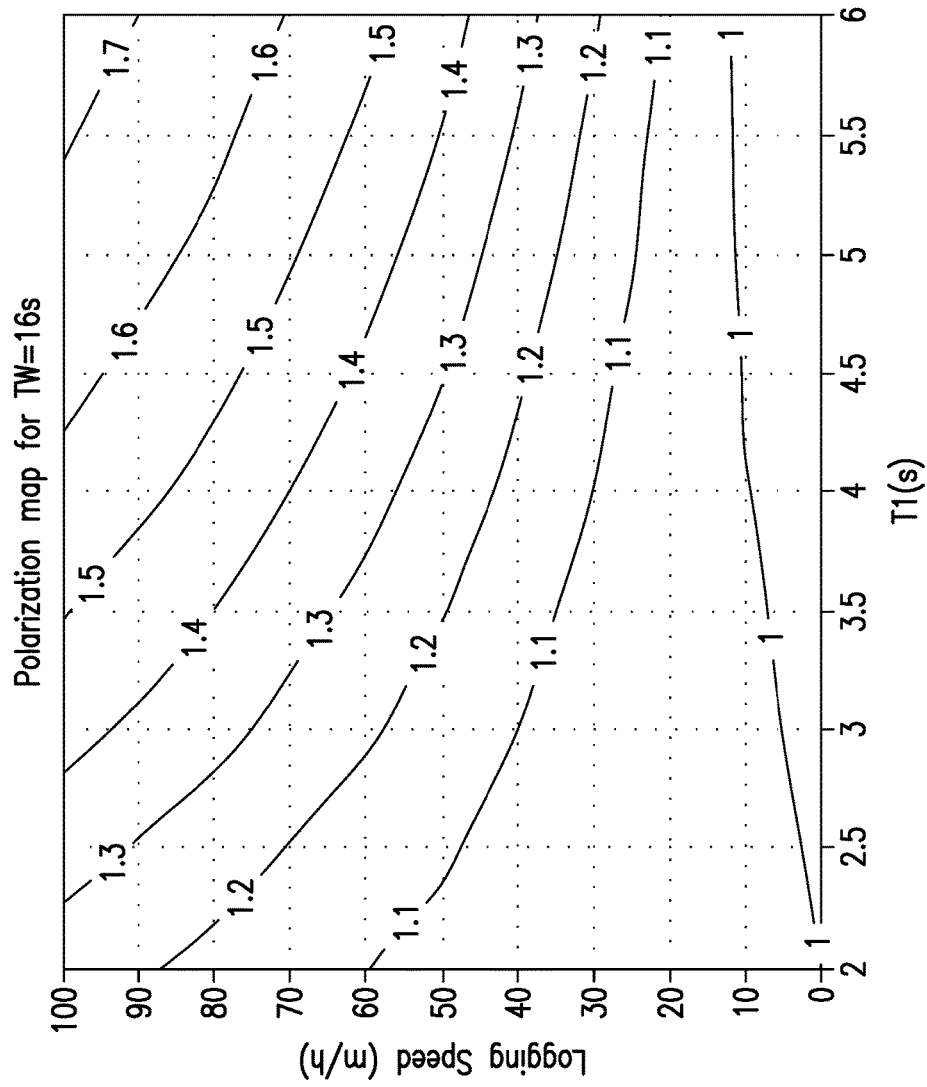
FIG. 2 depicts an example of a polarization map.

FIG. 2 shows an example of a polarization map that shows the polarization factor as function of logging speed and $T_{1\lambda}$ for a given tool design and a wait time of 16 seconds. The polarization map may be determined by modeling or based on empirical data (e.g., previous measurements or experimental data). The polarization factor is a dimensionless value that represents the polarization, where a value of one indicates full polarization or 100% polarization.

Failure to consider the logging speed can result in inaccurate measurements as well as inefficiencies. By failing to consider the logging speed for the selection of the wait time used in an NMR measurement, formation properties estimated from the NMR measurements can be inaccurate. For example, the measured porosity can be too large at elevated logging speeds. In addition, a wait time computed using only $T_{1\lambda}$ can be unnecessarily long. This translates into a loss of vertical resolution.

Embodiments described herein, which consider the logging speed in determination of the wait time, are effective in reducing or eliminating the enhanced-polarization effect, thereby producing more accurate results and eliminating or reducing the need for correction.

An example of the enhanced-polarization effect is discussed with reference to FIG. 2. In this example, a wait time of 16 is selected. As shown by the polarization map of FIG. 2, if $T_{1\lambda}$ is 5 seconds and the logging speed is 50 m/h, then the polarization will be 135%, i.e., the polarization factor of the long-$T_1$ porosity will be 1.35. NMR data collected using this wait time during this logging speed will result in a porosity overcall. The NMR data can be corrected for the polarization effect, however a large correction is perceived as a drawback.

The enhanced-polarization effect can be corrected, thus the system and/or processor may be configured to perform a polarization correction if necessary or desired. An example of a polarization correction is described in U.S. Pat. No. 7,196,516 to Blanz et al., issued Mar. 27, 2007, the entire contents of which are incorporated by reference herein. However, the embodiments described herein are able to select wait times sufficient to fully or sufficiently polarize a volume of interest, thus in some embodiments a polarization correction is not needed.

The processing device is configured to estimate or select the wait time in a number of ways. In one embodiment, a plurality of pre-defined wait times are selected, and each wait time is analyzed to determine whether the wait time satisfies a condition, which in one embodiment is related to an expected polarization. The shortest wait time that satisfies the condition is selected as the wait time (i.e., the long wait time) that is used in an NMR measurement.

In one embodiment, the system receives input parameters that include $T_{1\lambda}$, a target polarization (e.g., at least 95%), and an expected or planned logging speed. The target polarization may be a single value or a range of values. The expected polarization is computed for a plurality of pre-defined wait times. For each pre-defined wait time, an expected polarization is calculated based on $T_{1\lambda}$, the wait time and the logging speed. In one embodiment, a polarization map and/or curve is generated for each pre-defined wait time. Examples of pre-defined wait times include 6 second, 12 second and 16 second wait times.

The expected polarization for each wait time is compared to the target polarization, and the shortest pre-defined wait time that satisfies the condition that the expected polarization is larger than the target polarization or closest to 100% polarization is selected as the wait time to be used. Alternatively, the pre-defined wait time corresponding to a polarization that is closest to the target polarization is selected as the wait time.

An example of a choice (e.g., a default value) for a targeted polarization is at or about 95%. This polarization value has several advantages. It can be achieved even at very low logging speeds (no need to complicate the software implementation by additional if-clauses), it leads to acceptable wait times at low logging speeds (good for vertical resolution), and it is sufficiently close to 100% polarization. If the polarization is close enough to 100%, the polarization correction is small and can be avoided while still providing uncorrected data of acceptable accuracy. Avoidance of polarization correction can increase the speed of processing and is useful, e.g., for real time data acquisition and analysis.

In one embodiment, the processing device is configured to receive input parameters that include $T_{1\lambda}$, the target polarization, and an expected or planned logging speed. The processing device calculates a raw wait time as a function of $T_{1\lambda}$, the target polarization and the expected or planned logging speed. The wait time may be selected as the raw wait time, or a number of pre-defined wait times are compared to the raw wait time and the shortest predefined wait time that is larger than the raw wait time is selected as the wait time to be used for a pulse sequence. If the raw wait time is larger than the longest predefined wait time, then the longest predefined wait time may be selected as the wait time.

It is noted that selection of wait times can occur prior to performing an operation or during the operation. In one embodiment, the processing device is configured to receive input data including the logging speed in real time, and calculate or select the wait time in real time. For example, measurements of the logging speed (ROP) of a drilling assembly and/or measurements of the logging speed of a NMR tool are received at the processing device (which may be at the surface or downhole), and the processing device determines a wait time and transmits the wait time to the NMR tool transmitter via wired pipe, mud pulse or another suitable telemetry technique.

Figure 3:
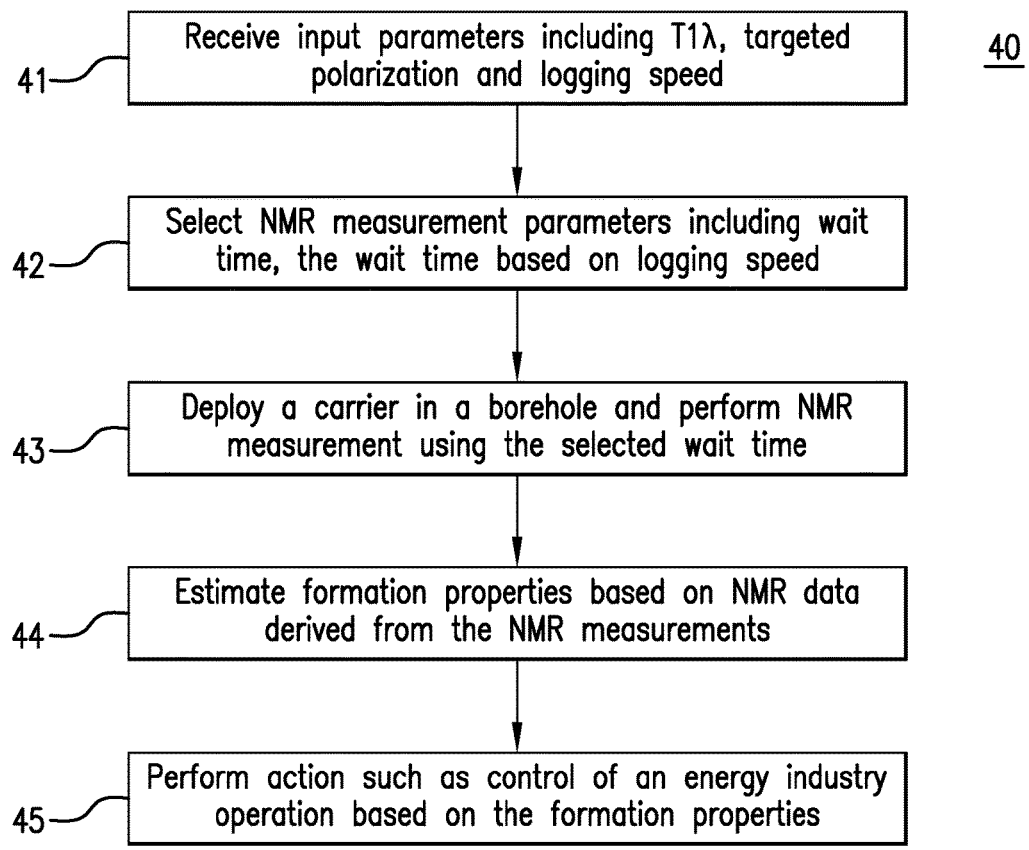
FIG. 3 is a flow chart depicting an embodiment of a method of performing an NMR measurement that includes selecting or estimating a pulse sequence wait time based on logging speed.

FIG. 3 illustrates a method 40 for performing an NMR measurement operation that includes estimation of motion and/or correction of NMR data based on estimations of motion. The method 40 may be performed in conjunction with the system 10, but is not limited thereto. The method 40 includes one or more of stages 41-45 described herein, at least portions of which may be performed by a processing device or processor (e.g., the surface processing unit 28). In one embodiment, the method 40 includes the execution of all of stages 41-45 in the order described. However, certain stages 41-45 may be omitted, stages may be added, or the order of the stages changed.

Figure 4:
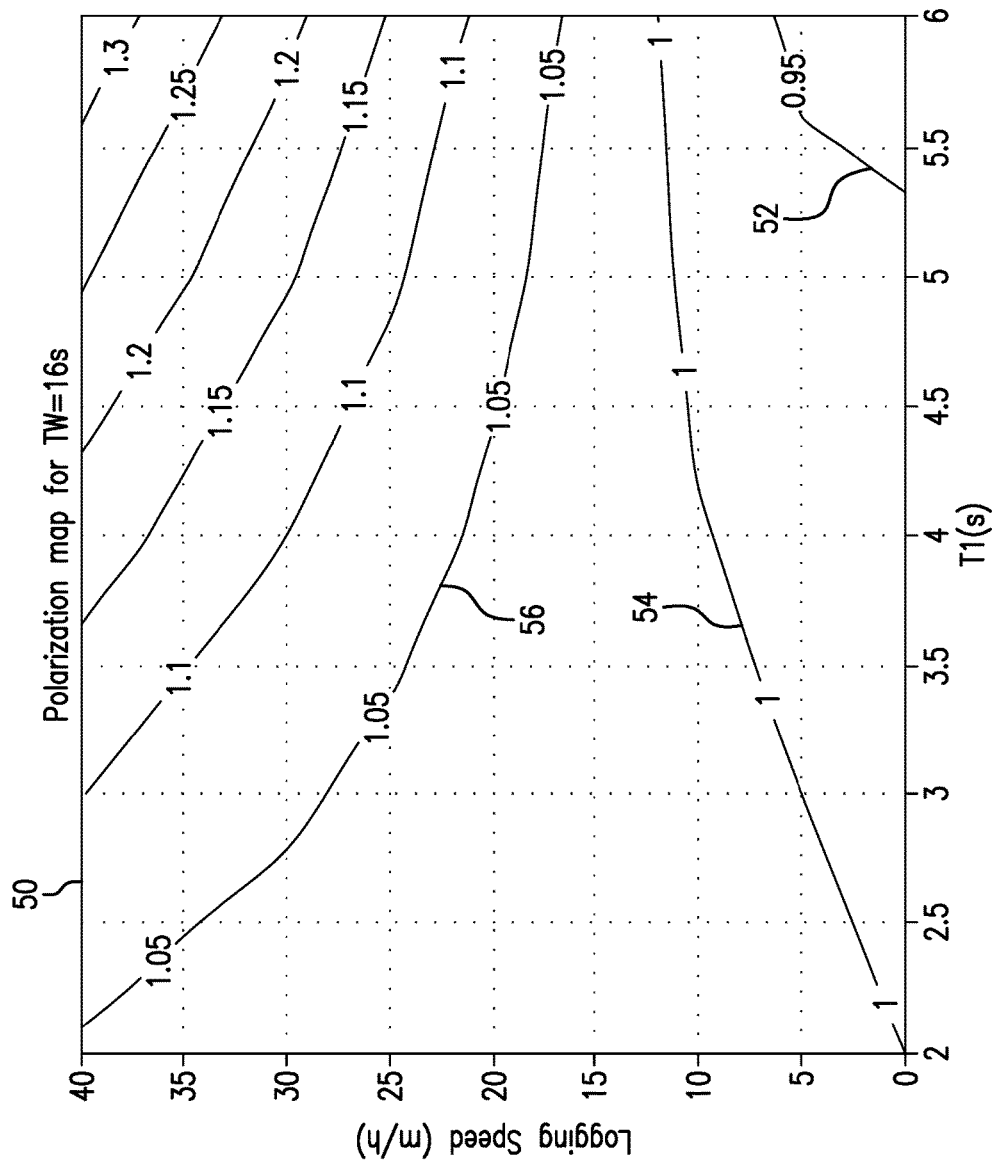
FIG. 4 depicts an example of a polarization map generated for a pre-defined wait time.
Figure 5:
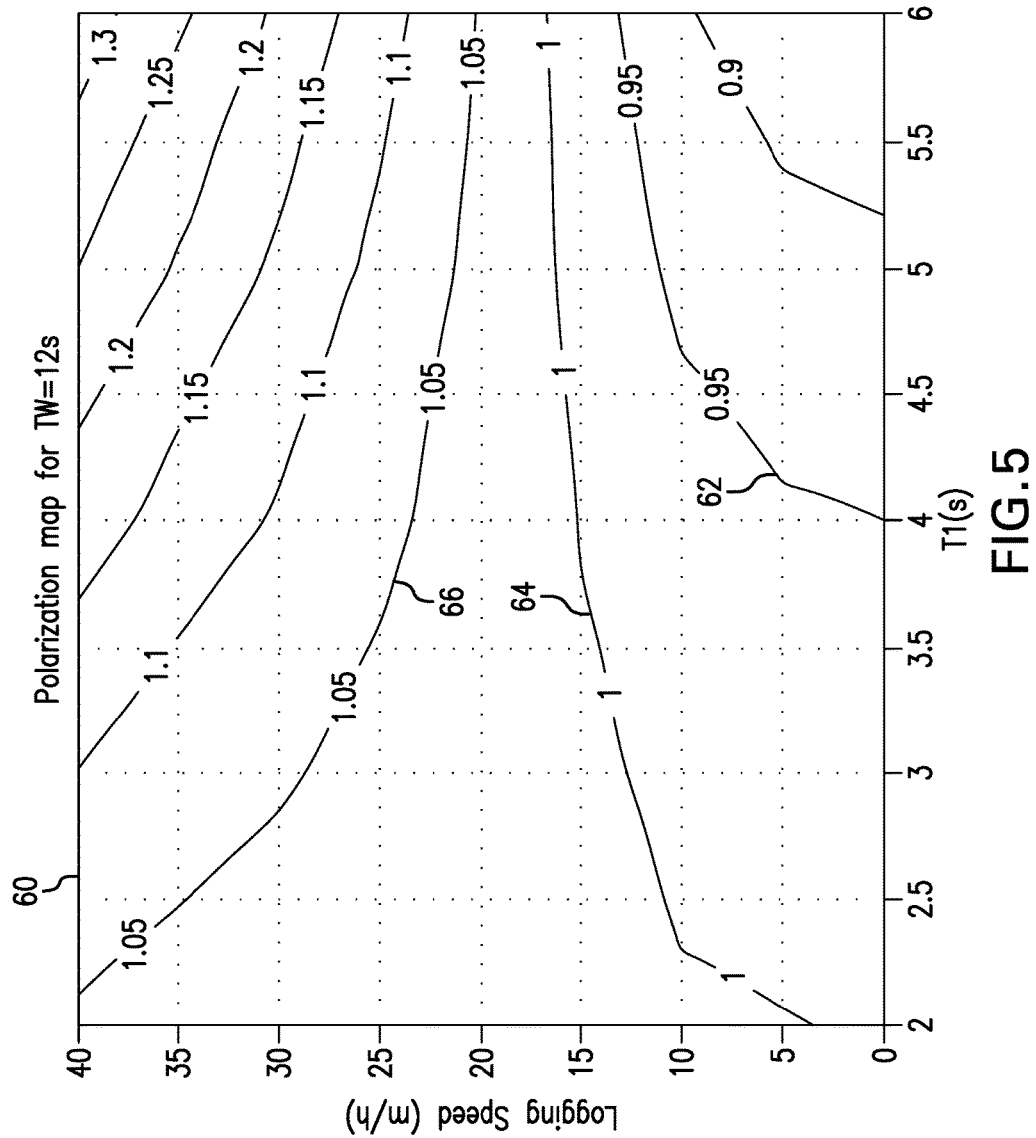
FIG. 5 depicts an example of a polarization map generated for a pre-defined wait time.
Figure 6:
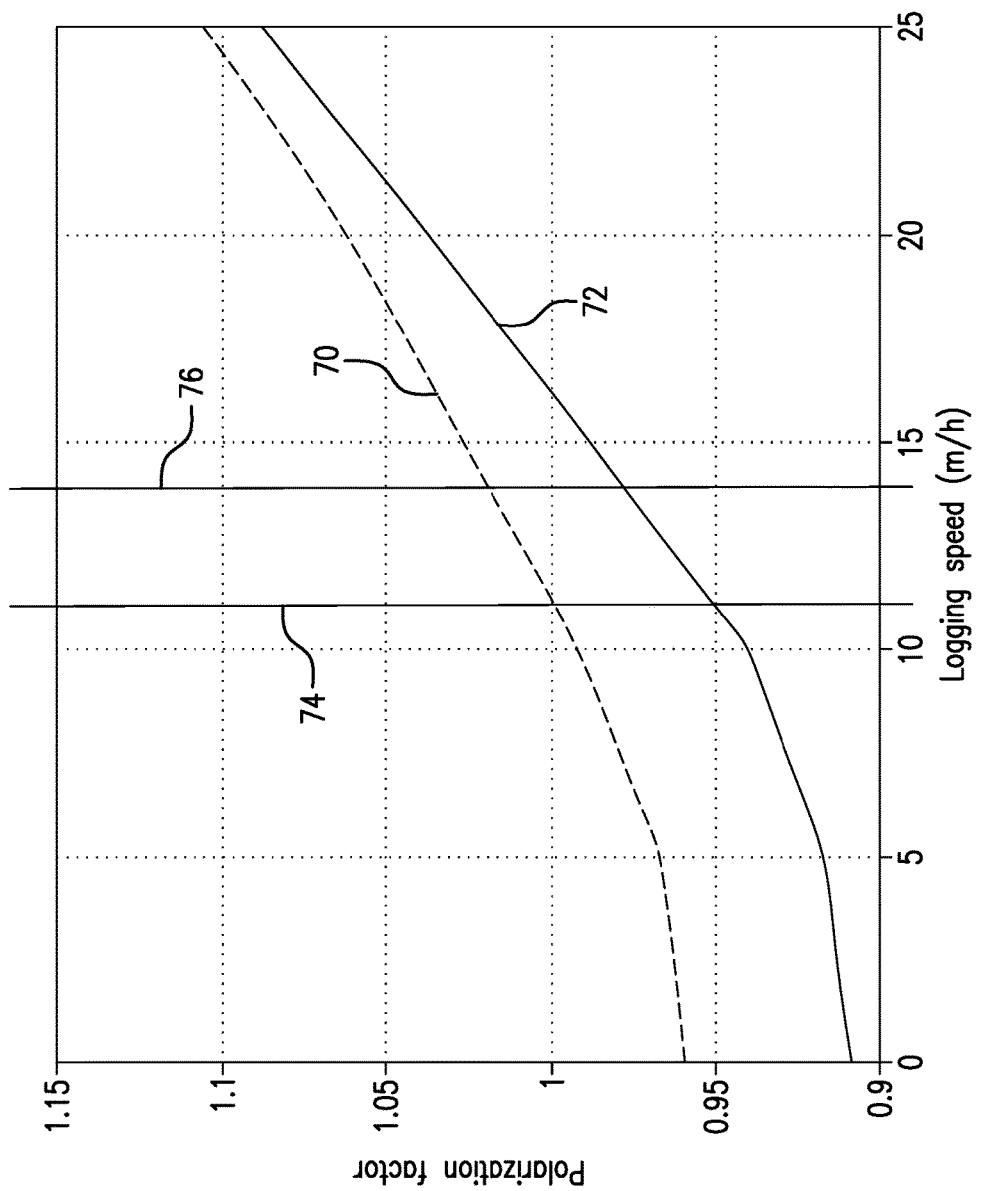
FIG. 6 depicts an example of polarization data in the form of polarization curves representing polarization as a function of logging speed.

The method 40 is described in conjunction with examples of polarization data shown in FIGS. 4-6. These examples are provided for illustration purposes; the method 40 is not limited to any particular wait time, fluid property or logging speed.

In the first stage 41, input parameters are received by a processing device, and a long wait time value is calculated. The input parameters include the $T_1$ value for a long-$T_1$ fluid ($T_{1\lambda}$), a targeted polarization and a logging speed value or range. The logging speed may be a measured logging speed (e.g., for calculation of TW during tool operation) or an expected or planned logging speed (e.g., for calculation of TW prior to performing a NMR acquisition).

In the second stage 42, NMR measurement parameters are received and/or estimated. The parameters include pulse sequence parameters such as pulse duration and inter-echo time. One of the parameters is the wait time, which is estimated or selected based on the $T_{1\lambda}$ value and the logging speed of an NMR tool.

In one embodiment, the processor receives a $T_{1\lambda}$ value, a target polarization, and a logging speed (e.g., an expected or planned logging speed, or a measured logging speed). The expected polarization is computed for a plurality of pre-defined wait times as a function of $T_{1\lambda}$, the pre-defined wait time and the logging speed.

For example, a logging speed value such as 15 meters per hour (m/h) is received or measured, and a $T_{1\lambda}$ value of 5 seconds is received. The processing device receives pre-defined wait times of 12 seconds and 16 seconds. The pre-defined wait times may be default values or values selected by a user.

The processing device generates or receives polarization data for the 16 second wait time in the form of a polarization map 50 shown in FIG. 4, which shows polarization curves representing different polarization factors in conjunction with logging speed and $T_1$. For example, curve 52 represents combinations of $T_1$ and logging speed that produce a 95% polarization (a polarization factor of 0.95) at 16 seconds. Curves 54 and 56 represent combinations that produce a 100% polarization and a 105% polarization, respectively.

The processing device also generates or receives polarization data for the 12 second wait time in the form of a polarization map 60 shown in FIG. 5, which shows polarization curves including a curve 62 representing combinations of $T_1$ and logging speed that produce a 95% polarization at 12 seconds. Curves 64 and 66 represent combinations that produce a 100% polarization and a 105% polarization, respectively.

The expected polarization for each wait time is estimated and analyzed with respect to a condition related to polarization. For example, the expected polarization is compared to a target polarization (e.g., 95%). The wait time to be used with a long measurement pulse sequence is selected as the wait time that produces a polarization that is larger than the target polarization or closest to 100%.

In the example described above, the expected polarization for a 16 second wait time based on a $T_{1\lambda}$ value of 5 seconds and a logging speed of 15 m/h is between 100% and 105%. The expected polarization for a 12 second wait time is between 95% and 100%. The wait time of 12 seconds is thus selected for use in the long pulse sequence.

In the third stage 43, the NMR tool is deployed into a borehole. In one embodiment, the tool (e.g., the tool 14) is deployed as part of a wireline operation, or during drilling as part of an LWD operation. It is noted that this stage may be performed or initiated prior to selection of the wait time or concurrently with stages 41 and/or 42.

Measurements are performed by generating a static magnetic field $B_0$ in a volume of interest in the formation, and transmitting a pulsed signal from at least one transmitting antenna according to one or more pulse sequences. In one embodiment, the pulse sequences are CPMG pulse sequences. At least one pulse sequence is a long sequence having the wait time that was selected or estimated based on $T_{1\lambda}$ and the logging speed of the NMR tool. Each pulse sequence generates an oscillating magnetic field $B_1$ in the volume of interest. At least one receiving antenna detects NMR signals from the volume in response to the interaction between the nuclear spins of interest and the static and oscillating magnetic fields, and generates raw NMR data. The raw NMR data include spin echo trains that may be measured at a plurality of depths.

The NMR measurement may include pulse sequences in addition to the long pulse sequence. For example, the pulse sequences also include a clay bound water (CBW) measurement which includes one or more CBW sequences. A CBW sequence is a sequence having a wait time corresponding to the $T_1$ value for clay bound water.

In the fourth stage 44, measured data including raw echo trains are processed to, e.g., remove noise and improve analysis, and analyzed to estimate formation properties. For example, processing includes an optional despiking (spike noise removal) of the measured data. Another example of processing includes calibration to correlate data values with fluid and/or formation property values. For example, the measured data (spin echo trains) are multiplied by a calibration factor to transform arbitrary units into porosity units. Other processing techniques include, for example, filtering to remove incomplete measurements, and phase rotating the data into a "signal channel".

An optional outflow correction may be applied to the processed NMR data. In one embodiment, an "outflow correction" corresponds to the "motion correction A" described in U.S. Pat. No. 7,358,725, which is incorporated herein by reference in its entirety. The outflow correction might be due to axial and/or radial movement of the tool.

Various properties may be estimated or derived based on the raw or processed NMR data. For example, the NMR data is analyzed to estimate the porosity of the volume of interest and estimate properties of fluid in the formation. Porosity information may be derived by analyzing the amplitudes of the porosity data and/or by estimating $T_2$ and/or $T_1$ values. For example, a fit of an exponential function to the NMR data is employed to estimate $T_2$ or porosity.

In the fifth stage 45, aspects of an energy industry operation are performed based on the properties of the formation. Examples of an energy industry operation include drilling, stimulation, formation evaluation, measurement and/or production operations. For example, the formation properties are used to plan a drilling operation (e.g., trajectory, bit and equipment type, mud composition, rate of penetration, etc.) and may also be used to monitor the operation in real time and adjust operational parameters (e.g., bit rotational speed, fluid flow).

FIG. 6 shows another example of polarization data, which shows polarization values as a function of logging speed for a number of different wait times. This data demonstrates how selection of the wait time based on logging speed can result in more accurate NMR measurements with a shorter wait time than is conventionally selected. In conventional NMR measurements the wait time is typically selected as 16 seconds. However, as demonstrated in FIG. 6, selection of a shorter wait time than that typically selected can be more accurate, or at least as accurate, as the typically selected wait time.

In this example, curve 70 represents a polarization factor as function of logging speed for a fluid having a $T_{1\lambda}$ of 5 seconds for a wait time of 16 seconds. Curve 72 shows the polarization factor for a wait time of 12 seconds. The vertical line 74 indicates a threshold at which the polarization is more than 95% for the wait time of 12 seconds. The vertical line 76 indicates a threshold at which an NMR measurement with a wait time of 12 seconds is more accurate than the measurement with a wait time of 16 seconds.

The apparatuses, systems and methods described herein provide numerous advantages. The embodiments described herein provide the ability to produce more accurate raw NMR data (e.g., porosity data) than prior art techniques and systems. As a result, polarization errors may be sufficiently small, which allows polarization correction techniques to be potentially avoided. In addition, the embodiments can lead to a significantly shorter wait time than the prior art. A shorter wait time directly translates into an improved vertical resolution.

Embodiment 1 A nuclear magnetic resonance (NMR) apparatus for estimating properties of an earth formation, the apparatus comprising: a carrier configured to be deployed in a borehole in the earth formation; an NMR measurement device including a transmitting assembly configured to emit a pulse sequence, and a receiving assembly configured to detect an echo train based on the pulse sequence; and a processor configured to communicate with the NMR measurement device, the processor configured to perform: receiving input parameters including an axial speed of the NMR measurement device and a $T_1$ value associated with a selected formation fluid; analyzing polarization data associated with the $T_1$ value, the polarization data describing a dependency between polarization and axial speed; determining a wait time for the pulse sequence based on the polarization data, and applying the pulse sequence with the determined wait time to the transmitting assembly; and estimating a property of the earth formation based on the echo train detected by the receiving assembly in response to the pulse sequence.

Embodiment 2 The apparatus of any prior embodiment, wherein the wait time is selected based on a long-$T_1$ fluid, the long-$T_1$ fluid selected from at least one of light oil, hydrocarbon gas and moveable water.

Embodiment 3 The apparatus of any prior embodiment, wherein the polarization data includes a polarization map that represents polarization values as a function of axial speeds and $T_1$ values.

Embodiment 4 The apparatus of any prior embodiment, wherein analyzing includes estimating an expected polarization for at least one of a plurality of pre-defined wait times, and determining includes selecting one of the plurality of pre-defined wait times based on comparing the expected polarization to a selected condition.

Embodiment 5 The apparatus of any prior embodiment, wherein determining includes selecting the shortest pre-defined wait time that satisfies the selected condition as the wait time to be applied with the pulse sequence.

Embodiment 6 The apparatus of any prior embodiment, wherein determining includes selecting the pre-defined wait time that is associated with a polarization that is larger than a target polarization or closest to 100% polarization, as the wait time to be applied with the pulse sequence.

Embodiment 7 The apparatus of any prior embodiment, wherein the input parameters include an expected logging speed and a target polarization, and analyzing includes estimating a raw wait time based on the $T_1$ value and the expected logging speed.

Embodiment 8 The apparatus of any prior embodiment, wherein determining includes one of: selecting a wait time that is equal to or related to the raw wait time; and selecting one of a plurality of pre-defined wait times, the selected pre-defined wait time being the shortest pre-defined wait time that is larger than the raw wait time.

Embodiment 9 The apparatus of any prior embodiment, wherein the processor is configured to receive at least the axial speed and determine the wait time in real time during an energy industry operation.

Embodiment 10 The apparatus of any prior embodiment, wherein the NMR measurement device is a low gradient NMR device.

Embodiment 11 A method of performing a nuclear magnetic resonance (NMR) measurement, the method comprising: receiving input parameters at a processor in communication with an NMR measurement device, the input parameters including an axial speed of the NMR measurement device and a $T_1$ value associated with a selected formation fluid, the NMR measurement device including a transmitting assembly configured to emit a pulse sequence into an earth formation; analyzing polarization data associated with the $T_1$ value, the polarization data describing a dependency between polarization and axial speed; determining a wait time for the pulse sequence based on the polarization data, and applying the pulse sequence with the determined wait time to the transmitting assembly; and estimating a property of the earth formation based on an echo train detected by the NMR measurement device in response to the pulse sequence.

Embodiment 12 The method of any prior embodiment, wherein the wait time is selected based on a long-$T_1$ fluid, the long-$T_1$ fluid selected from at least one of light oil, hydrocarbon gas and moveable water.

Embodiment 13 The method of any prior embodiment, wherein the polarization data includes a polarization map that represents polarization values as a function of axial speeds and $T_1$ values.

Embodiment 14 The method of any prior embodiment, wherein analyzing includes estimating an expected polarization for at least one of a plurality of pre-defined wait times, and determining includes selecting one of the plurality of pre-defined wait times based on comparing the expected polarization to a selected condition.

Embodiment 15 The method of any prior embodiment, wherein determining includes selecting the shortest pre-defined wait time that satisfies the selected condition as the wait time to be applied with the pulse sequence.

Embodiment 16 The method of any prior embodiment, wherein determining includes selecting the pre-defined wait time that is associated with a polarization that is larger than a target polarization or closest to 100% polarization, as the wait time to be applied with the pulse sequence.

Embodiment 17 The method of any prior embodiment, wherein the input parameters include an expected logging speed and a target polarization, and analyzing includes estimating a wait time based on the $T_1$ value and the expected logging speed.

Embodiment 18 The method of any prior embodiment, wherein the input parameters include an expected logging speed, a target polarization and an initially selected wait time, and determining includes one of: selecting a wait time that is equal to or related to the raw wait time; and selecting one of a plurality of pre-defined wait times, the selected pre-defined wait time being the shortest pre-defined wait time that is larger than the raw wait time.

Embodiment 19 The method of any prior embodiment, wherein receiving at least the axial speed and determining the wait time is performed in real time during an energy industry operation.

Embodiment 20 The method of any prior embodiment, wherein the NMR measurement device is a low gradient NMR device.

In connection with the teachings herein, various analyses and/or analytical components may be used, including digital and/or analog subsystems. The system may have components such as a processor, storage media, memory, input, output, communications link (wired, wireless, pulsed mud, optical or other), user interfaces, software programs, signal processors and other such components (such as resistors, capacitors, inductors, etc.) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user, or other such personnel, in addition to the functions described in this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention.

What is claimed is:

1. A nuclear magnetic resonance (NMR) apparatus for estimating properties of an earth formation, the apparatus comprising:
a carrier configured to be deployed in a borehole in the earth formation;
an NMR measurement device including a transmitting assembly configured to emit a pulse sequence, and a receiving assembly configured to detect an echo train based on the pulse sequence; and
a processor configured to communicate with the NMR measurement device, the processor configured to perform:
receiving input parameters including an axial speed of the NMR measurement device and a $T_1$ value associated with a selected formation fluid;
analyzing polarization data associated with the $T_1$ value, the polarization data describing a dependency between polarization and axial speed;
determining a wait time for the pulse sequence based on the polarization data, and applying the pulse sequence with the determined wait time to the transmitting assembly; and
estimating a property of the earth formation based on the echo train detected by the receiving assembly in response to the pulse sequence.

2. The apparatus of claim 1, wherein the wait time is selected based on a long-$T_1$ fluid, the long-$T_1$ fluid selected from at least one of light oil, hydrocarbon gas and moveable water.

3. The apparatus of claim 1, wherein the polarization data includes a polarization map that represents polarization values as a function of axial speeds and $T_1$ values.

4. The apparatus of claim 1, wherein analyzing includes estimating an expected polarization for at least one of a plurality of pre-defined wait times, and determining includes selecting one of the plurality of pre-defined wait times based on comparing the expected polarization to a selected condition.

5. The apparatus of claim 4, wherein determining includes selecting the shortest pre-defined wait time that satisfies the selected condition as the wait time to be applied with the pulse sequence.

6. The apparatus of claim 4, wherein determining includes selecting the pre-defined wait time that is associated with a polarization that is larger than a target polarization or closest to 100% polarization, as the wait time to be applied with the pulse sequence.

7. The apparatus of claim 1, wherein the input parameters include an expected axial speed and a target polarization, and analyzing includes estimating a raw wait time based on the $T_1$ value and the expected axial speed.

8. The apparatus of claim 7, wherein determining includes one of:
selecting a wait time that is equal to or related to the raw wait time; and
selecting one of a plurality of pre-defined wait times, the selected pre-defined wait time being the shortest pre-defined wait time that is larger than the raw wait time.

9. The apparatus of claim 1, wherein the processor is configured to receive at least the axial speed and determine the wait time in real time during an energy industry operation.

10. The apparatus of claim 1, wherein the NMR measurement device is a low gradient NMR device.

11. A method of performing a nuclear magnetic resonance (NMR) measurement, the method comprising:
receiving input parameters at a processor in communication with an NMR measurement device, the input parameters including an axial speed of the NMR measurement device and a $T_1$ value associated with a selected formation fluid, the NMR measurement device including a transmitting assembly configured to emit a pulse sequence into an earth formation;
analyzing polarization data associated with the $T_1$ value, the polarization data describing a dependency between polarization and axial speed;
determining a wait time for the pulse sequence based on the polarization data, and applying the pulse sequence with the determined wait time to the transmitting assembly; and
estimating a property of the earth formation based on an echo train detected by the NMR measurement device in response to the pulse sequence.

12. The method of claim 11, wherein the wait time is selected based on a long-$T_1$ fluid, the long-$T_1$ fluid selected from at least one of light oil, hydrocarbon gas and moveable water.

13. The method of claim 11, wherein the polarization data includes a polarization map that represents polarization values as a function of axial speeds and $T_1$ values.

14. The method of claim 11, wherein analyzing includes estimating an expected polarization for at least one of a plurality of pre-defined wait times, and determining includes selecting one of the plurality of pre-defined wait times based on comparing the expected polarization to a selected condition.

15. The method of claim 14, wherein determining includes selecting the shortest pre-defined wait time that satisfies the selected condition as the wait time to be applied with the pulse sequence.

16. The method of claim 14, wherein determining includes selecting the pre-defined wait time that is associated with a polarization that is larger than a target polarization or closest to 100% polarization, as the wait time to be applied with the pulse sequence.

17. The method of claim 11, wherein the input parameters include an expected axial speed and a target polarization, and analyzing includes estimating a wait time based on the $T_1$ value and the expected axial speed.

18. The method of claim 11, wherein the input parameters include an expected axial speed, a target polarization and an initially selected wait time, and determining includes one of:
selecting a wait time that is equal to or related to a raw wait time; and
selecting one of a plurality of pre-defined wait times, the selected pre-defined wait time being the shortest pre-defined wait time that is larger than the raw wait time.

19. The method of claim 11, wherein receiving at least the axial speed and determining the wait time is performed in real time during an energy industry operation.

20. The method of claim 11, wherein the NMR measurement device is a low gradient NMR device.

* * * * *